US007890349B2

(12) United States Patent
Cole et al.

(10) Patent No.: US 7,890,349 B2
(45) Date of Patent: Feb. 15, 2011

(54) RESOURCE MONITORING SYSTEM FOR PROCESSING LOCATION RELATED INFORMATION IN A HEALTHCARE ENTERPRISE

(75) Inventors: Douglas J. Cole, Valley Forge, PA (US); Ilene Sue Yost, Collegeville, PA (US); Mike Digiacomo, Douglasville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2212 days.

(21) Appl. No.: 10/113,703

(22) Filed: Apr. 1, 2002

(65) Prior Publication Data
US 2003/0078811 A1 Apr. 24, 2003

Related U.S. Application Data

(60) Provisional application No. 60/337,876, filed on Oct. 22, 2001.

(51) Int. Cl.
*G06F 19/00* (2011.01)
(52) U.S. Cl. .......................................................... 705/3
(58) Field of Classification Search .................. 705/2–3
See application file for complete search history.

(56) References Cited

U.S. PATENT DOCUMENTS

| 5,065,315 | A | * | 11/1991 | Garcia | 705/2 |
|---|---|---|---|---|---|
| 5,291,399 | A | * | 3/1994 | Chaco | 705/3 |
| 5,732,401 | A | * | 3/1998 | Conway | 705/29 |
| 5,991,728 | A | | 11/1999 | Debusk et al. | 705/2 |
| 6,014,633 | A | * | 1/2000 | DeBusk et al. | 705/7 |
| 6,073,110 | A | * | 6/2000 | Rhodes et al. | 705/8 |
| 6,223,164 | B1 | | 4/2001 | Seare et al. | 705/2 |
| 6,314,556 | B1 | * | 11/2001 | DeBusk et al. | 717/107 |
| 2001/0016821 | A1 | | 8/2001 | DeBusk et al. | 705/2 |
| 2002/0013714 | A1 | * | 1/2002 | Dubler et al. | 705/2 |
| 2003/0074222 | A1 | * | 4/2003 | Rosow et al. | 705/2 |

OTHER PUBLICATIONS

MediNous @ www.medinous.com. Copyright 1996.*
Jaikumar Vijayan. "'Clean Slat' Approach Smooths Medical Care" Apr. 13, 1998. Computerworld. vol. 32, Iss. 15. p. 37.*
Express Healthcare Management @ www.expresshealthcaremgmt.com/20010930/hrd2.htm. Sep. 30, 2001. Iss. 16.*
Z. Bliznakov. "An Integrated Software System for Medical Equipment Management" Copyright 2001.*
Moshe Zviran, PhD. "Defining the Application Portfolio for an Integrated Hospital Information System: A Tutorial" 1990. Journal of Medical Systems. vol. 14, Nos. ½. p. 31.*
William Pierskalla and Diedre Woods. "Computers in Hospital Management and Improvements in Patient Care—New Trends in the United States" 1988. Journal of Medical Systems. vol. 12, No. 6. p. 411.*
Sally McClean and Peter H. Millard. "A Decision Support System for Bed-Occupancy Management and Planning Hospitals" @ http://imamb.oxfordjournals.org./cgi/content/abstract/12/3-4/249. 1995.*
The Room-Bed Master, Aug. 1990.

* cited by examiner

*Primary Examiner*—Dilek B Cobanoglu
(74) *Attorney, Agent, or Firm*—Alexander J Burke

(57) ABSTRACT

A system supports creation and modification of a flexible and comprehensive location structure model able to track patients in a healthcare (or other) setting and identify suitable patient locations and location availability via a user friendly display interface. A method processes location related information for use in facilitating movement of a patient in a healthcare enterprise. The method involves establishing a profile comprising information identifying multiple locations available to accommodate a patient for different purposes. The profile incorporates attributes including a location type identifier, and a location characteristic of clinical significance influencing availability of a particular location to a patient having a particular medical condition. The profile is employed in providing a user with an indication of location availability in response to user command.

25 Claims, 10 Drawing Sheets

Searching your hierarchy

Use these options to search the active location hierarchy.

705 — Within an encounter location: [▼]

707 — Within a location group: [▼]

Searching for

Use these options with the hierarchy options or separately to focus your search.

709 — Category: [▼]

711 — Type: [▼]

713 — Clinical service: [▼]
☐ Main  ☐ Primary  ☐ Secondary

715 — Charge category: [▼]

717 — Availability change: [▼]

719 — Reason: [▼]

721 — From: [🗓]  Through: [🗓]

723 — Level of care: [▼]

725 — Name: [▼]

727 — System ID: [▼]  ☐ Exact match

729 — Patient location features:
☐ Private location
☐ Recommended for VIPs
☐ Gender designation
  ○ For female patients only
  ○ For male patients only

Find a location

Search by:

Name: [ 3 ] ▶ ☐ Exact match — 902

Category: [ Patient location ] ▶ — 904

Type: [ ] ▶ — 906

Service provider organization: [ ] ▶ — 908

Clinical service: [ ] ▶ — 910
☐ Main ☐ Primary ☐ Secondary

Gender designation — 913
⊙ None
○ For female patients only
○ For male patients only Results: (105 found - you might want to narrow your criteria) — 920

| Location name | Type |
|---|---|
| 3West Pre-op | Ward |
| 3West Recovery | Ward |
| 3West Surgery | Ward |
| 301 | Private room |
| 302A | Bed |
| 302B | Bed |
| 303A | Bed |
| 303B | Bed |
| 304A | Bed |
| 304B | Bed |
| 305A | Bed |
| 305B | Bed |
| 306 | Private room |
| 307A | Bed |
| 307B | Bed |

Details: — 923
304A
Max. 1 occupant(s)
Normal level/care: Xxxxxx
Clinical services: Med/Surg, Orthopedics, Oncology

[ Go search ] [ Clear search ] 🔍 — 925   [ Add new ] [ Cancel ]

900

US 7,890,349 B2

RESOURCE MONITORING SYSTEM FOR PROCESSING LOCATION RELATED INFORMATION IN A HEALTHCARE ENTERPRISE

This is a non-provisional application of provisional application Ser. No. 60/337,876 by Douglas J. Cole et al., filed Oct. 22, 2001. This application is concurrently filed with commonly owned related application Ser. No. 10/113,091 Entitled "A Resource Monitoring and User Interface System for Processing Location Related Information in a Healthcare Enterprise,".

FIELD OF THE INVENTION

This invention concerns a system and user interface for processing location related information for use in facilitating movement of a patient in a healthcare enterprise, for example.

BACKGROUND OF THE INVENTION

Modern healthcare requires the provision of services to patients by many health-care workers at a multiplicity of locations. In order to accomplish this, healthcare delivery is organized into specialized departments such as nursing, laboratory, radiology, pharmacy, surgery, emergency, administrative and other departments which are variously located at one or more sites. The management of these locations involves accumulating, processing and maintaining large quantities of information. This information is used in determining location availability, location suitability for a patient with particular medical conditions, billing for location occupancy as well as for patient tracking and other purposes. Consequently, there is a need for a computerized system capable of defining and maintaining location information for a health care enterprise and for supporting healthcare system operation by defining, processing and filtering location information for presentation to users and other system software applications.

Available healthcare location information management systems have limited capabilities and numerous deficiencies. Specifically, available systems are typically restricted in location structure models that are supported. In one such system, a lowest level location in a structure is constrained to be a patient bed that is in a room that is part of a nurse station, for example. Further, this lowest level location is considered to hold one and only one patient at a time. In addition, available systems typically require significant user intervention and Online Architecture System (OAS) coding to activate or deactivate locations in a location structure model. Similarly, such systems do not facilitate user friendly, timely modification and modification tracking of an existing location structure model. Available systems also conventionally provide limited capability to track patients in a healthcare enterprise. A patient assigned to a room as an inpatient, is not tracked if in a waiting room or another department for services (such as radiology for an xray), for example. A system according to invention principles addresses these deficiencies and derivative problems.

SUMMARY OF INVENTION

A system supports creation and modification of a flexible and comprehensive location structure model able to track patients and identify suitable patient locations and location availability via a user friendly display interface. A method processes location related information for use in facilitating movement of a patient in a healthcare enterprise. The method involves establishing a profile comprising information identifying multiple locations available to accommodate a patient for different purposes. The profile incorporates attributes including a location type identifier, and a location characteristic of clinical significance influencing availability of a particular location to a patient having a particular medical condition. The profile is employed in providing a user with an indication of location availability in response to user command.

BRIEF DESCRIPTION OF THE DRAWING

FIG. 9 shows a user interface display image menu supporting a user search for a location within a particular location structure model including a comprehensive set of search prompt elements, according to invention principles.

FIG. 10 shows a composite user interface display image supporting a user search for a location within a particular location structure model in a first window and location search results in a second window, according to invention principles.

DETAILED DESCRIPTION OF INVENTION

Figure 1:
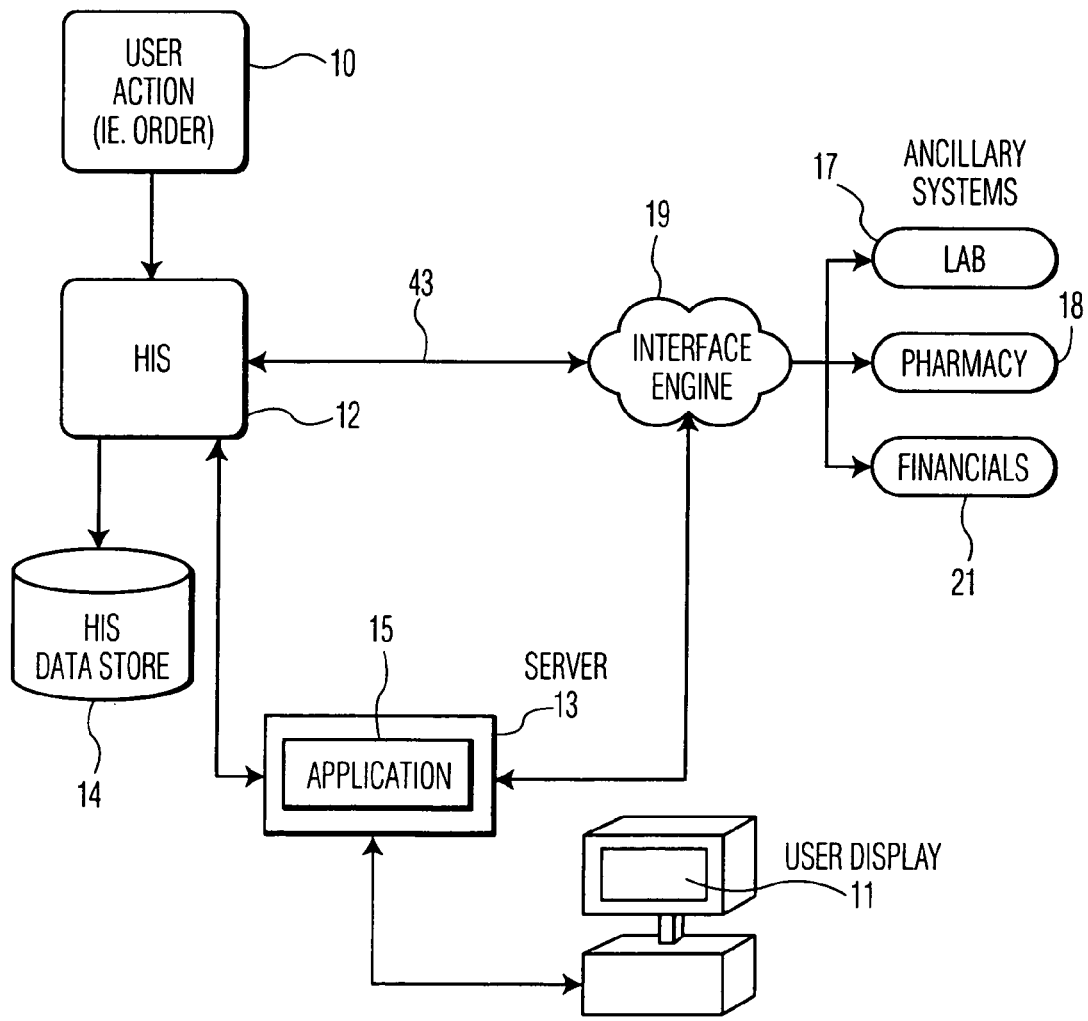
FIG. 1 shows a healthcare enterprise employing a location management information system, according to invention principles.

FIG. 1 shows a healthcare enterprise employing a location management information system. The location management information system supports creation, management and modification of a profile comprising information identifying a hierarchical organization of locations available to accommodate a patient. The locations defined may comprise grouped locations or an individual location for hosting a patient encounter with a healthcare enterprise involving patient and healthcare enterprise interaction or for accommodating a patient for other purposes. Following definition of locations and their characteristics, the system supports a user in organizing the locations into a hierarchy, representing their physical structure. The location hierarchy and associated information comprises a profile that facilitates patient tracking and business processes by identifying patient locations (existing ones and those planned for the future), and generating charges based on level of care and charge category and other characteristics, for example.

A created hierarchical profile minimizes user maintenance of the created location hierarchy when additional locations become available or when existing locations require renovations or temporary closing. A profile is also advantageously associated with a date thereby permitting identification of prior location structures for the purpose of patient charge verification following a structure alteration, for example, and for other purposes. Within a profile, locations are defined based on their physical organization (such as "beds" within "rooms", "rooms" within "nurse stations" or "clinics" etc.). The profile advantageously shows the relationship between individual locations that are available for assignment for a patient related activity.

A user is able to define a hierarchical (parent-child) relationship between locations within a profile location structure and the location structure represents physically existing locations. For example, if a wing is added to a hospital, the wing and all of its components (e.g. nurse stations, rooms, and beds etc.) are defined as locations in the hierarchical profile structure. The definition indicates the existence of the locations and does not indicate whether the locations are available for assignment to a patient activity. The availability of a location for scheduled assignment for a patient activity is advantageously supported outside of the hierarchical structure. Thereby, a user may employ the location profile to schedule use of locations to be opened at a later time (such a section of a wing of a hospital, for example) without requiring a new location hierarchy to be created that includes the planned (but as yet uncompleted) locations. Further, a profile location structure is able to advantageously incorporate locations external to a health system. Such external locations include, for example, locations where a patient may be referred to, such as a lab work facility for conducting patient tests, for example.

A location profile is advantageously time and date stamped to indicate a location structure maintained at a particular point in time. Previous profiles reflecting structures prior to alteration, for example, are also retained. This enables patient locations and associated costs to be tracked in obsolete or no longer existing building configurations and structures and supports accurate billing and historical record keeping. A location profile also advantageously enables definition of a patient location supporting multiple occupants. This allows a room to be classified as a patient location and house many patients, for example. This is a common occurrence when the particular bed a patient occupies in a room is unimportant such as in a nursery or in a "holding area" awaiting an inpatient location.

In the FIG. 1 healthcare enterprise, a location management information system is embodied in application 15 executing on server 13 and accessed by remote PC and associated user interface 11. The location management information system bidirectionally communicates with Healthcare Information System (HIS) 12 employing patient record repository 14 in processing user actions 10 such as treatment related orders including medication preparation orders, for example. In addition Location management application 15 and HIS 12 bidirectionally communicate with external systems 17-21 through an interface engine 19. Interface engine 19 may comprise a workflow processing application or other application supporting communication with external systems 17-21. External systems 17-21 comprise a laboratory 17, pharmacy 18 and financial application (such as for patient service tracking and billing) 21, for example, but may also encompass a broader range of systems including any system with which HIS 12 performs a transaction or data exchange. Further Healthcare Information System (HIS) 12 may comprise other types of information system such as a Clinical Information System or Critical Care Information System or another Information system. In other embodiments location management application 15 may reside in other types of enterprise including non-healthcare information systems involving location management for tracking people goods or services.

Figure 2:
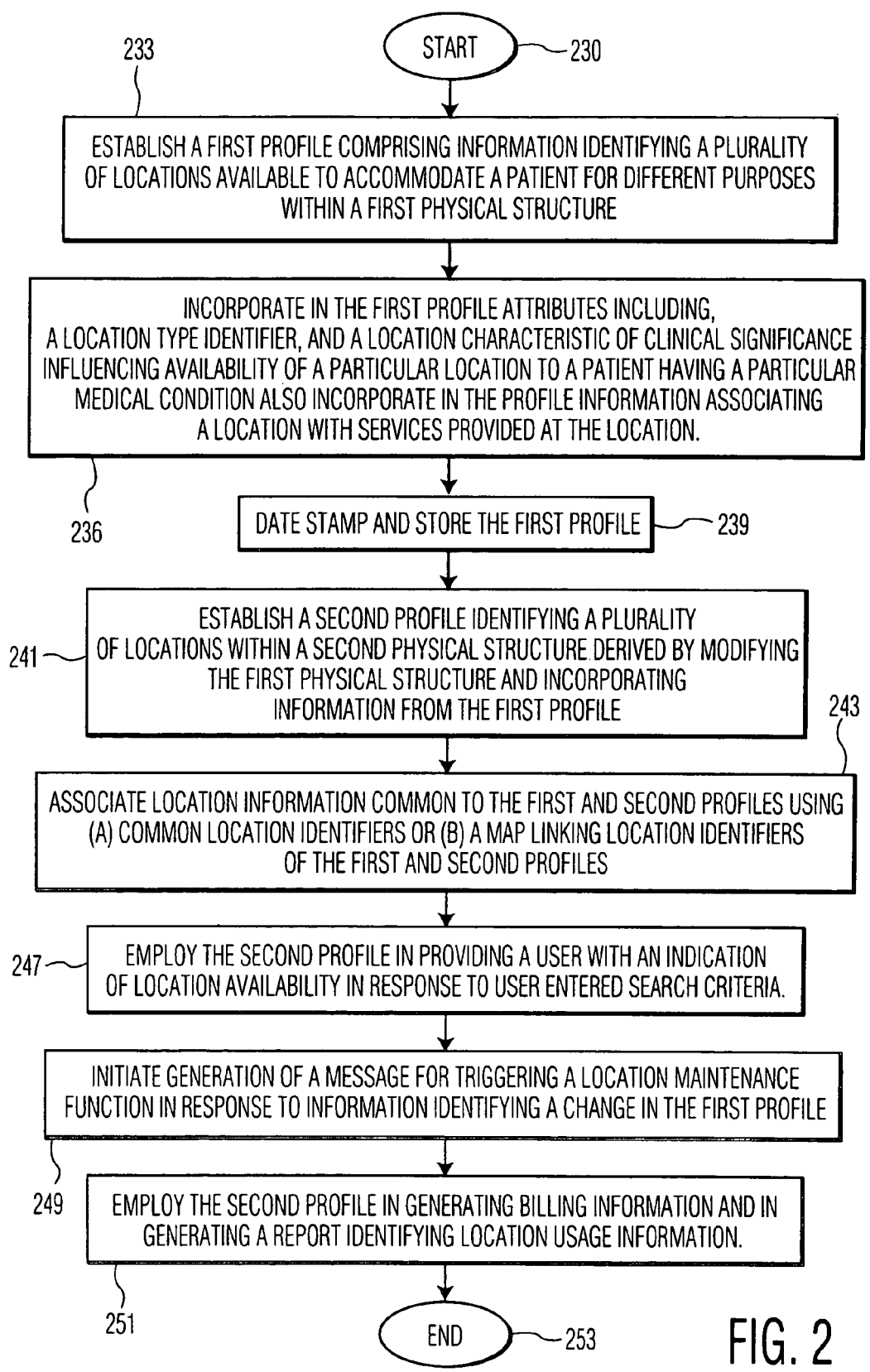
FIG. 2 shows a flowchart of a process employed by the location management information system of FIG. 1 in presenting searching and processing location information, according to invention principles.

FIG. 2 shows a flowchart of a process employed by the location management application 15 of FIG. 1 in creating, maintaining, searching, processing and presenting location information in response to user command. In step 233 after the start at step 230, application 15 supports user creation and maintenance of a first profile comprising information identifying a hierarchical structure of locations available to accommodate a patient for different purposes. The location first profile may be freshly created or may be derived by editing an existing profile stored in a master file. Application 15 supports the following profile creation and editing functions for this purpose.

I. Location Definition
  A. Select Location Master File
    1. Add new location
      a) Location Group
        Grouping of other locations
        Association of the location group to the appropriate Encounter Location
        Association of the location group to the locations that make up the group
      b) Encounter Location
        May host patient encounters
        Has physical address
        May be associated with one or more appropriate service providers (Health Provider Organizations)
      c) Patient Locations
        Lowest level of individual location
        Identify maximum occupancy
          1 occupant
          Multiple occupants
        Support for availability types and reasons (e.g. location is "out of service" due to "renovations")
        Support for multiple clinical services tied to a location, including multiple primary and multiple secondary
    2. Location basics & details
      phones associated with a location
      addresses tied to an encounter location
      reporting attribute information
      type code (a user defined code to classify the locations for reporting or census purposes)
      Type code examples include:
        Room
        Bed
        Chairs
        Bassinets
        Nursery
        Waiting area
        Hallway bed
        Exam room
        Treatment room
        Recovery room
      name (short, long, alias)
      default level of care
      accommodation types/attributes II. Define Hierarchical Structure
   A. Location Hierarchy
      1. Hierarchical maintenance to facilitate creation of physical location structure:
         Edit item details
         Validate hierarchy
         Remove item from hierarchy
         Add item to hierarchy
         Move item within hierarchy III. Location Management
   A. Find Location for patient tracking & maintenance
   B. Automatic Triggers for housekeeping when room is dirty
   C. Charge generation based on charge category and/or level of care and other parameters
   D. Reporting for analysis and process improvement Note, a patient encounter encompasses any event whereby a patient interacts with a healthcare enterprise and includes inpatient or outpatient visits, phone calls to a doctor, registration, treatment activity, billing etc.

A hierarchical location profile created by application 15 indicates a relationship between individual physically existing locations supporting patient assignment. A particular location is incorporated in a hierarchical profile in order to track consequences of the physical use of the particular location. Locations in the hierarchy may be date and time stamped for availability at a future date enabling a location profile to advantageously accurately reflect a structure incorporating locations due to open at different future times. For example, a user may incorporate in a profile particular nurse station locations scheduled for future availability and specify that these stations are out of service until particular respective future dates. Locations may be indicated as unavailable for a variety of other reasons including, for example, being under construction or requiring maintenance. Application 15, in response to user command, is able to override an indicated location unavailability. Further, a location (such as a location hosting patient encounters) does not need to be in the hierarchy unless it is desired to track patients there or to assign patients there. In addition, a location in a hierarchical profile may also be used outside this particular profile.

In response to user command, application 15 uses its profile creation and editing functions in step 236 (FIG. 2) to associate a location with services available at the location and to incorporate location type characteristics and location characteristics of clinical significance. This is done to advantageously facilitate user selection of an appropriate location for a particular patient. Location type characteristics identify a location such as a patient room, a hospital waiting room, a hospital department room, a surgery related room, a location within an identified room, an identified room in an identified building of a healthcare enterprise and a location outside a healthcare enterprise. Hospital departments include, for example, radiology, laboratory, pharmacy, patient clinical examination, test and evaluation, administration, nursing, outpatient and emergency departments. The location characteristics of clinical significance influence availability of a location to a patient with a particular medical condition and include information identifying a level of care category associated with a location. Such levels of care include the following predetermined levels of care, for example:

Acute—Patient requires nursing care on a regular basis; medical condition is currently stable. Patient normally does not require special medical equipment to sustain life. Medical encounter is normally of a short-term basis. (Normal Hospital In-patient).

Intensive Care—Patient requires constant nursing supervision and/or care. Patient medical condition is not stable. Patient may require medical equipment to sustain life. Medical encounter is of an unknown basis due to patient condition. (Hospital Intensive Care Patient, Cardiac Care Patient).

Emergency—Patient requires immediate medical attention, medical condition is presumed to be unstable. (Emergency Room Patient).

Trauma—Patient requires immediate, constant medical attention. Patients medical condition is life threatening. (Trauma Center Patient).

Observation—Patient requires nursing supervision on a consistent, periodic basis. Patient medical condition is stable but requires monitoring in order to determine if medical condition is improving or deteriorating. Observation status encounter is assumed to be of a short-term basis. (Hospital Observation Patient).

Skilled Nursing—Patient needs nursing assistance to perform normal daily activities. Medical condition is stable. These patients normal have a physical medical condition or are recovering from a medical condition, which limits their self-sufficiency. (Hospital, Nursing Home or Rehab Patient).

Intermediate Care—Patient needs intermittent nursing assistance but is relatively self sufficient and able to perform almost all daily activities themselves. Medical condition is normally stable. (Hospital, Nursing Home or Rehab Patient).

Long Term Care—Patient's medical condition is chronic and requires medical care or nursing assistance for an extended period of time. Medical condition is normally stable (Nursing Home or Rehab Patient).

In step 236 and in response to user command, application 15 associates a location with services available at the location including clinical services such as medical, surgical, obstetric/maternity, nursery, psychiatric and pediatric services. Application 15, in response to user command, also associates other characteristics and services with a particular location. Such other characteristics and services include, for example, Telemetry Indicator—an indicator as to whether the location is equipped for telemetry Oxygen Indicator—an indicator as to whether the location is equipped with oxygen Oversized Patient Accommodations Indicator—an indicator as to whether the location is equipped to handle large patients Child accommodations Indicator—an indicator as to whether the location is equipped as a child's room Traction Indicator—an indicator as to whether the location is equipped with traction equipment Video Monitoring Indicator—an indicator as to whether the location is equipped with video monitoring Mattress Type—specifies the type of mattress the location is equipped with.

Water Mattress

Air Mattress

Sand Mattress

Standard Mattress (default)

VIP Location Indicator—(Special private location with upgraded accommodations)—an indicator as to whether the location is equipped with upgraded accommodations for VIPs Privacy Indicator—this is an indicator as to whether the location is considered private or not—applies to patient locations with a maximum occupancy of 1. This indicator is used to filter locations for patient assignment and facilitates searches for private accommodations.

Yes—this is a private location

No—this is not a private location

Combining Gender Indicator—an indicator as to whether the location supports mixing patients of different genders. This indicator is only valid for patient locations with a maximum occupancy greater than 1.

Gender Code—specifies the specific gender of patients that can be assigned to the location. This handles the designation of male or female only locations. There is no processing in the system to prevent patient locations of different specific gender designations from being put together in location groups during location hierarchy definition. If no gender code is specified, there is no restriction.

Male only—only male patients should be assigned

Female only—only female patients should be assigned

Make Dirty Indicator—indicates that a location becomes dirty after a patient is removed from it. For single occupancy patient locations, the default is "Y". For multiple occupancy patient locations, the default is "N".

Age Range Preference—specifies the user-defined range of age that is most appropriate for the specific location. The allowable values for this are user defined ranges that must support different units, days, weeks, months, and years. For example, a location may be suited for infants so it would be defined with an age preference of <6 months versus a children's location that would be defined with an age preference of <18 years.

Charge Category Code—specifies the categorization of the location to facilitate charge generation and billing for the location. For example:

Private Room

Semi-Private—2 bed room

Semi-Private—3 & 4 Beds

Private Deluxe

Ward—5 or more beds

Other

Nursery

Coronary Care

Intensive Care

In steps 233 and 236 (FIG. 2) and responding to user command, application 15 uses its profile creation and editing functions to create profile database information for identifying locations able to host particular patient related activities and encounters as well as for identifying locations that a patient may occupy. Types of locations that are assigned include (a) an encounter location (typically a location where a patient is directed via an address), (b) a patient location (typically able to accommodate one or more patients) and (c) a location group (a physical grouping of patient locations). Further, under this type assignment a patient location may not be a location group. In contrast, a nurse station may be assigned to be a location group and be comprised of other location groups such as rooms. A location group may be further classified as an encounter location. An encounter location is usually associated with one or more Health Provider Organizations that may operate in the particular location. An encounter location may be a hospital where patients report to be checked-in for services, for example. An encounter location may also be a specific location such as a pharmacy, laboratory or a radiology clinic with a physical address where patients are sent for services to be performed. Areas within an encounter location may or may not be identified as being able to accommodate patients. An encounter location is able to be associated with a physical address for shipping goods or mailing and if they are the same a single address may be entered by a user.

In steps 233 and 236 (FIG. 2) and responding to user command, application 15 uses its profile creation and editing functions to create profile database information for identifying characteristics of locations. Such characteristics include location name (including both short and long versions), mnemonic, and associations with clinical services, levels of care, accommodation types and occupancy information. Patient locations such as waiting rooms or nurseries, for example, are typically usable by more than one occupant at a time and are able to be associated with characteristics identifying they are multiple occupancy locations and have a particular maximum occupancy limit. A location group is associated with a capacity parameter comprising a sum of the maximum occupancies of the individual locations encompassed within the location group for a given point in time since availability of a patient location may change.

Application 15 advantageously considers location availability in determining location capacity and adjusts its record of location capacity to reflect an out of service location within an encompassing location group. Such an out of service status may result from maintenance or renovation, for example. Further, location capacity or maximum occupancy is adjustable by a user on a temporary basis (e.g. for particular periods) or permanent basis. This may be done to reduce workload if nurses are absent by reducing maximum occupancy of a relevant location, for example. Alternatively, if there is an emergency situation, a user is able to increase the maximum occupancy of a location to handle an increase in workload for a period.

In step 239 (FIG. 2) in response to user command, application 15 validates and date and time stamps a created profile for storage in a database. Application 15 applies predetermined rules in validating a created or modified location profile. Such rules include, ensuring that, (i) a patient location is a child of a location group, (ii) a patient location does not have any subordinates, (iii) a particular location is not in a location profile more than once, (iv) a hierarchical location profile has a location group at its highest level and (v) a location group is not required to encompass a patient location. In another embodiment, different or additional validation rules may be applied. Further, application 15 date and time stamps the first profile to indicate a last date and a first date the profile is valid Application 15, in step 239, also date and time stamps a new association of a clinical service and a particular location. The date and time stamp may be a current or a future stamp to indicate, for example, a clinical service is to be provided at a location at a particular date (e.g. an office will begin to support a radiology clinical service effective Jan. 1, 2003). In the absence of a start date for a clinical service, application 15 assumes a service to have been continuously available. The date and time stamping of the association of services with a location advantageously enables tracking of patient charges and verification of billing information (e.g., by indicating a service could not have been provided to a patient on a specific date since it was unavailable at the time and location concerned).

In step 241 in response to user command, application 15 establishes a second profile incorporating information from the first profile created in step 233. The second profile comprises information identifying locations within a second physical structure derived by modifying the first physical structure. Further, the second profile is time and date stamped in similar fashion to the first profile. Application 15 in step 243 associates location information common to both first and second profiles using common location identifiers or a map linking location identifiers of the first profile to location identifiers of the second profile. In step 247 application 15 employs the second profile in finding information concerning a particular location in response to user entered search criteria. Further, in step 249 in response to a received message, application 15 initiates a first profile location maintenance function. Such a message identifies a change affecting the first profile such as a change in location availability, a change in location occupancy and a change in location condition, for example. In step 251, application 15 employs the second profile in generating billing information and in generating a report identifying location usage information for a particular patient. The process of FIG. 2 terminates at step 253.

Figure 3:
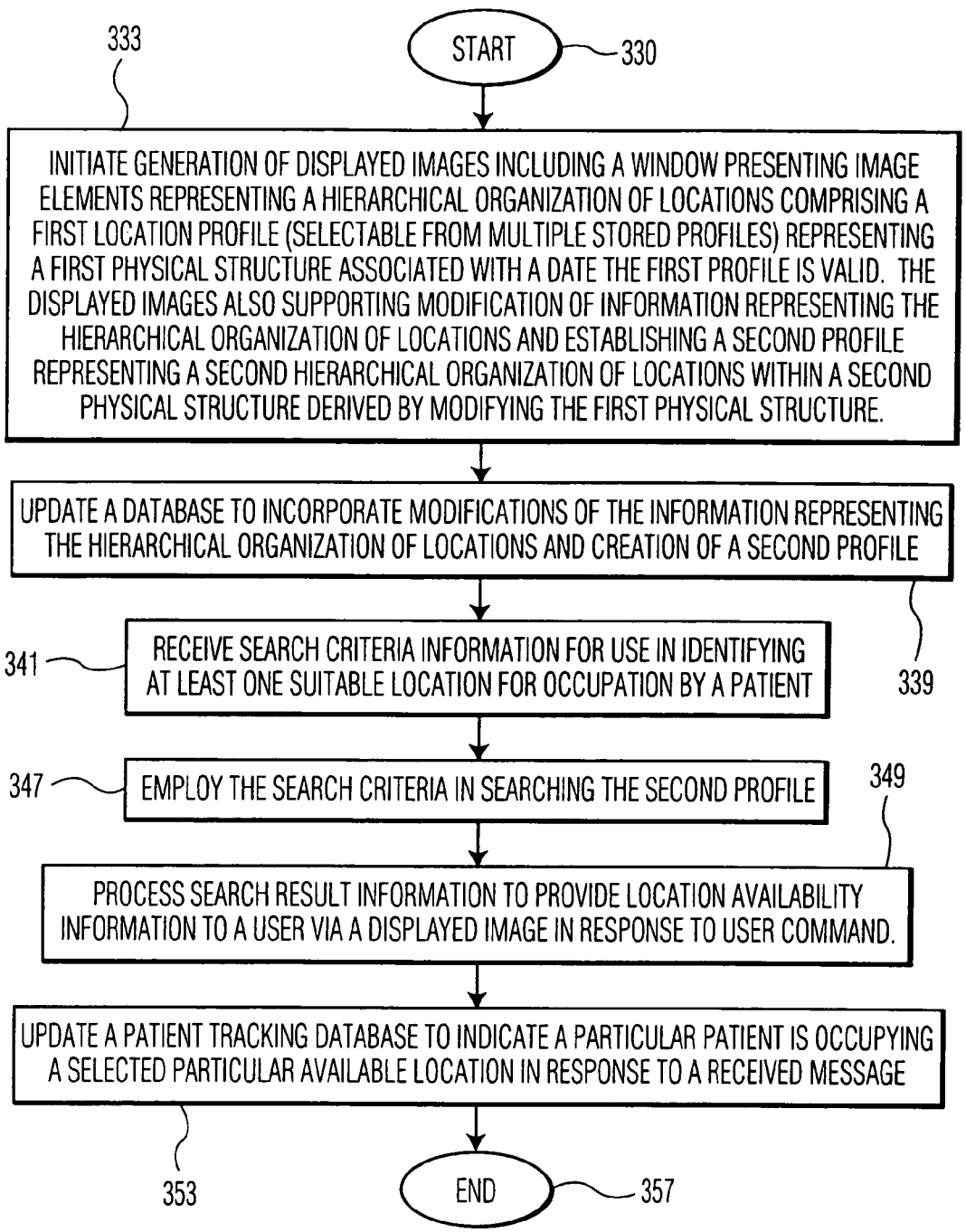
FIG. 3 shows a flowchart of a process for creating, modifying and maintaining a location profile within the location management information system of FIG. 1, according to invention principles.
Figure 4:
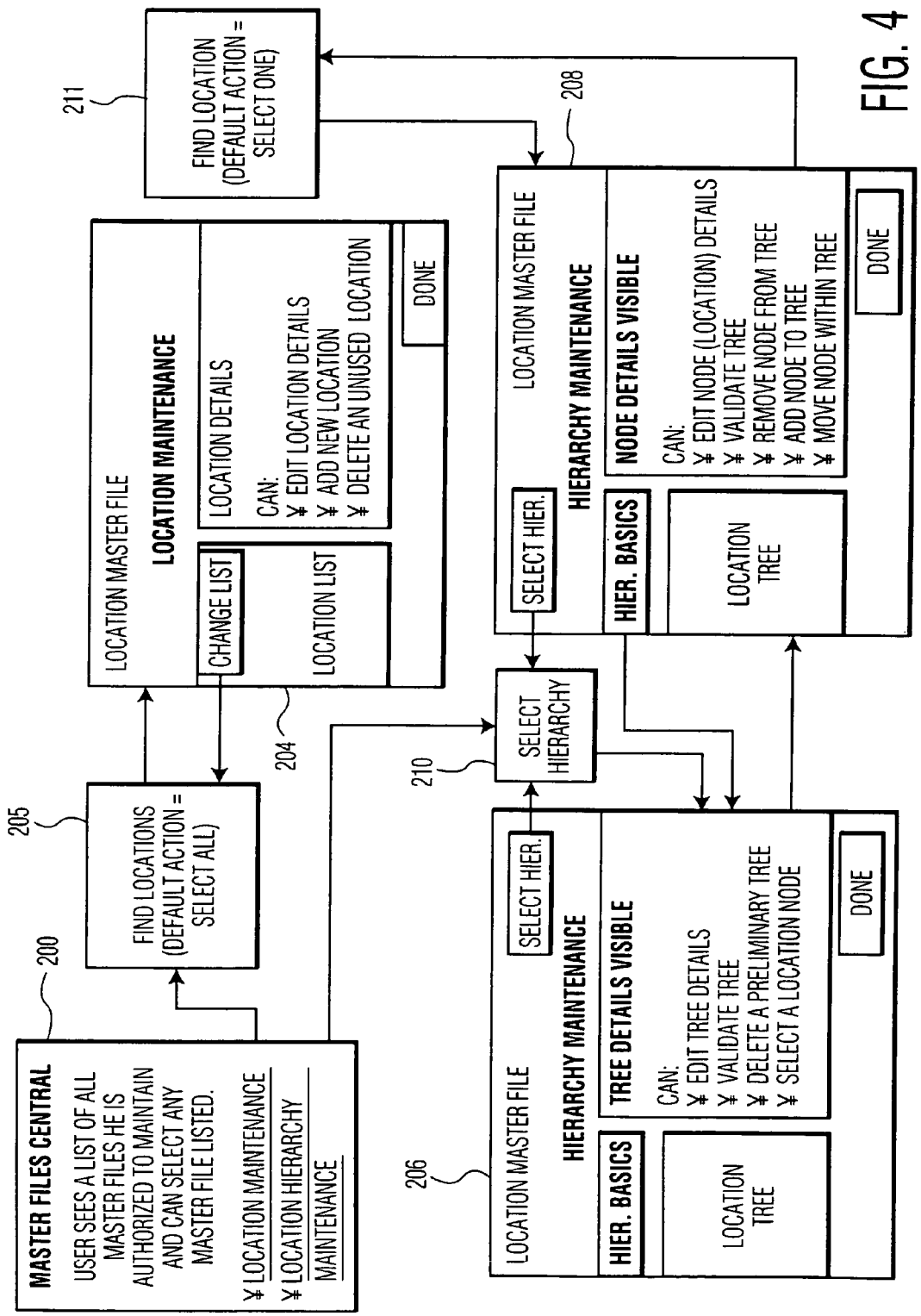
FIG. 4 shows a user interface display image navigation sequence supporting the location management information system, according to invention principles.

FIG. 3 shows a flowchart of a process for creating, modifying and maintaining a location profile within the location management information system of FIG. 1. In step 333 after the start at step 330, application 15 initiates generation of displayed images including a window presenting image elements representing a first location profile comprising a hierarchical structure of locations. The first location profile represents a corresponding physical structure and is associated with date and time stamps indicating a first time and date the profile was valid and, if appropriate, a last time and date the profile was valid. FIG. 4 shows a user interface display image navigation sequence supporting creation and editing of a location profile in step 333 of FIG. 3.

In response to user command, display image 200 of FIG. 4 is presented showing a list of master files containing data representing corresponding location profiles. Display image 200 includes at least one prompt element supporting user selection of a profile from multiple profiles with associated respective different dates of validity. Display image 200 is used to initiate creation and maintenance of a hierarchical location profile (via display images 206 and 208) or maintenance of location characteristics (via display image 204). A user may select (via image 200) a location profile master file in step 210 (FIG. 4) for viewing, editing and validation of a location hierarchical tree and associated tree details (e.g., for directly editing tree details) via display image 206. Similarly, a user may select (via image 200) a location profile master file in step 210 (FIG. 4) for viewing, editing and validation of a particular node (location representative item) and associated node characteristics within a hierarchical location tree (e.g., for removing or adding a node) via display image 208. Display image 208 also supports finding a location and associated node characteristics for viewing and editing in command step 211. In addition, image 200 supports finding a particular location or multiple locations associated with a particular profile (step 205) for viewing and editing of characteristics of individual locations (e.g., for adding or deleting details of a particular location such as services associated with the particular location) via display image 204.

Figure 6:
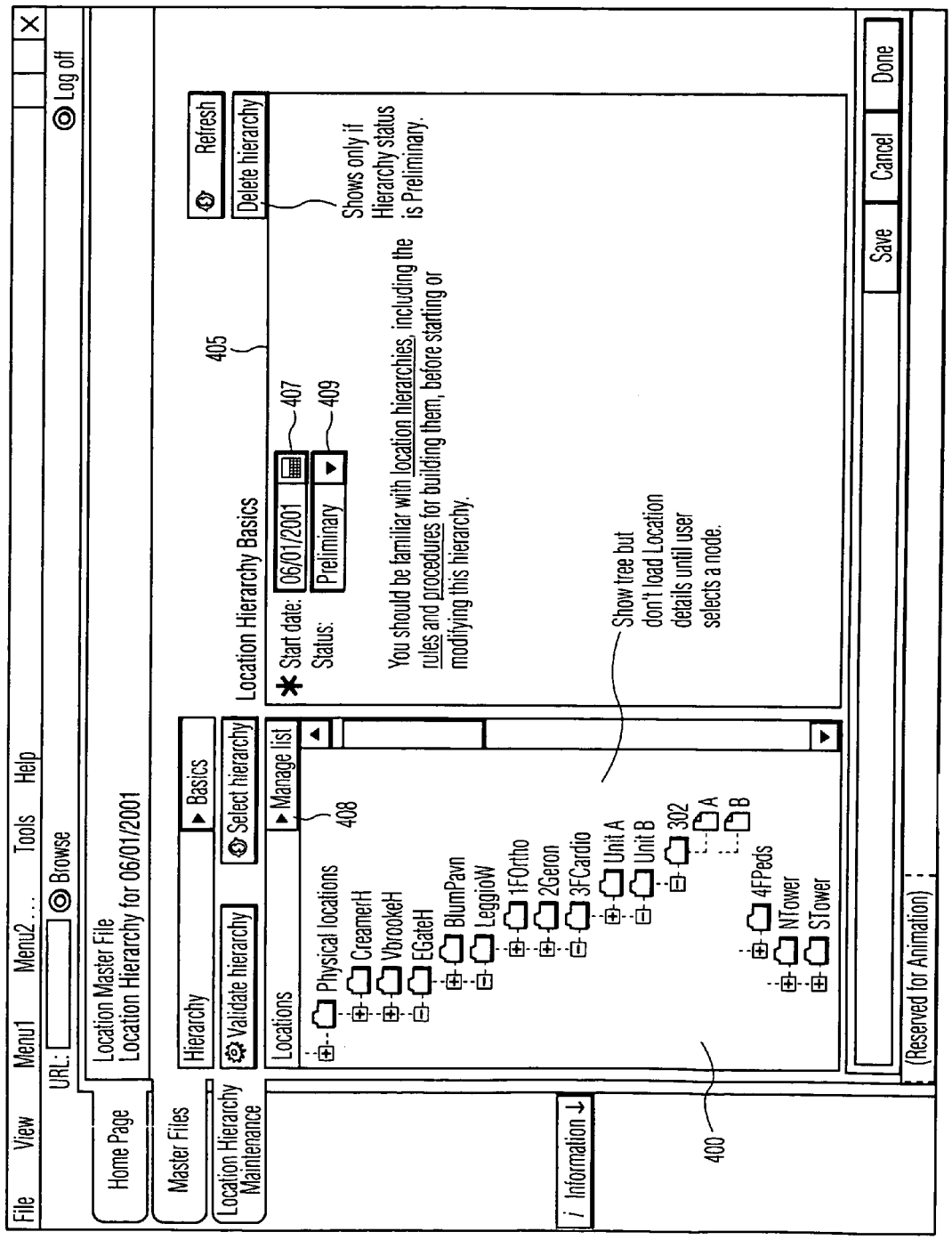
FIG. 6 shows a user interface display image supporting maintenance of a location structure model, according to invention principles.

FIG. 6 shows a user interface display image for use in maintaining a location profile of the type employed in display images 206 and 208 of FIG. 4, for example. The display image of FIG. 6 includes windows 400 and 405. Window 400 is used to indicate a currently selected hierarchical location profile structure in a tree format representation. Window 405 is used for showing characteristics of items selected in window 400 and for initiating editing and validation operations on the selected location profile or its selected items. Item 407 of window 405 indicates the currently selected location profile is valid from start date Jun. 1, 2001, for example. Item 409 indicates the currently selected location profile is of preliminary status and inactive.

The FIG. 6 image is displayed in response to user selection of a location hierarchy maintenance item (e.g., within image 200 of FIG. 4). In the absence of an existing location profile the FIG. 6 image display opens in an add mode presenting a blank node in window 400 with an edit cursor in start date field 407. A user accepts a default date (equal to current date plus one day) or enters a new date in item 407. A hierarchy status defaults to preliminary status and may not be changed until at least one node is entered. A user initiates creation of a location profile by selecting icon 408. If the FIG. 6 image display opens in response to selection of an existing location profile the structure of the profile is shown in window 400. For this to occur the location items comprising the profile hierarchy need to be already defined. Application 15 validates a created preliminary profile to prevent creation of multiple preliminary profiles of the same type with the same date. Multiple concurrent profiles of the same type and date but of different status (e.g., one preliminary and one active) are permitted.

A preliminary or active profile may be copied and used as the basis for modification and creation of a new profile which is given an initial default preliminary status. An item is added to a preliminary profile by selecting an existing item in a hierarchy and indicating whether a new item is to be inserted above, below, or at the same level as the selected item. A blank item is inserted at the desired point and a prompt is generated prompting a user to find an item for insertion. If a desired item is found, it is inserted to replace the blank item. If a desired item is not found a user may elect to add a new item (e.g., a location or other item) via a location or hierarchy profile maintenance menu (e.g. via display images 204, 206 or 208 of FIG. 4). Further, a preliminary hierarchy is validated in response to user command or automatically upon activation when a user makes a preliminary hierarchy active.

Returning to the flowchart of FIG. 3, application 15 in step 333 and in response to user command also initiates generation of displayed images (such as images 204, 206 or 208 of FIG. 4) including menus supporting modification of information representing the first location profile to derive a second profile representing a second physical structure. The menus support adding a location, removing a location, moving a location from a first position to a second position in the hierarchical organization of locations, editing characteristics of locations and validating an edited profile. In step 339, application 15 updates a database to incorporate data representing the second profile derived by modifying information representing the first profile.

Application 15, employs user entered search criteria received in step 341 in searching a database storing information representing the second profile in step 347 to determine availability of a location. In step 349 application 15 processes derived search result data to provide location availability information to a user via a displayed image. Application 15 updates a patient tracking database in step 353 to indicate a particular patient is occupying a selected particular location in response to a received indication that the patient is occupying the particular available location. The process of FIG. 3 ends at step 357.

Figure 5:
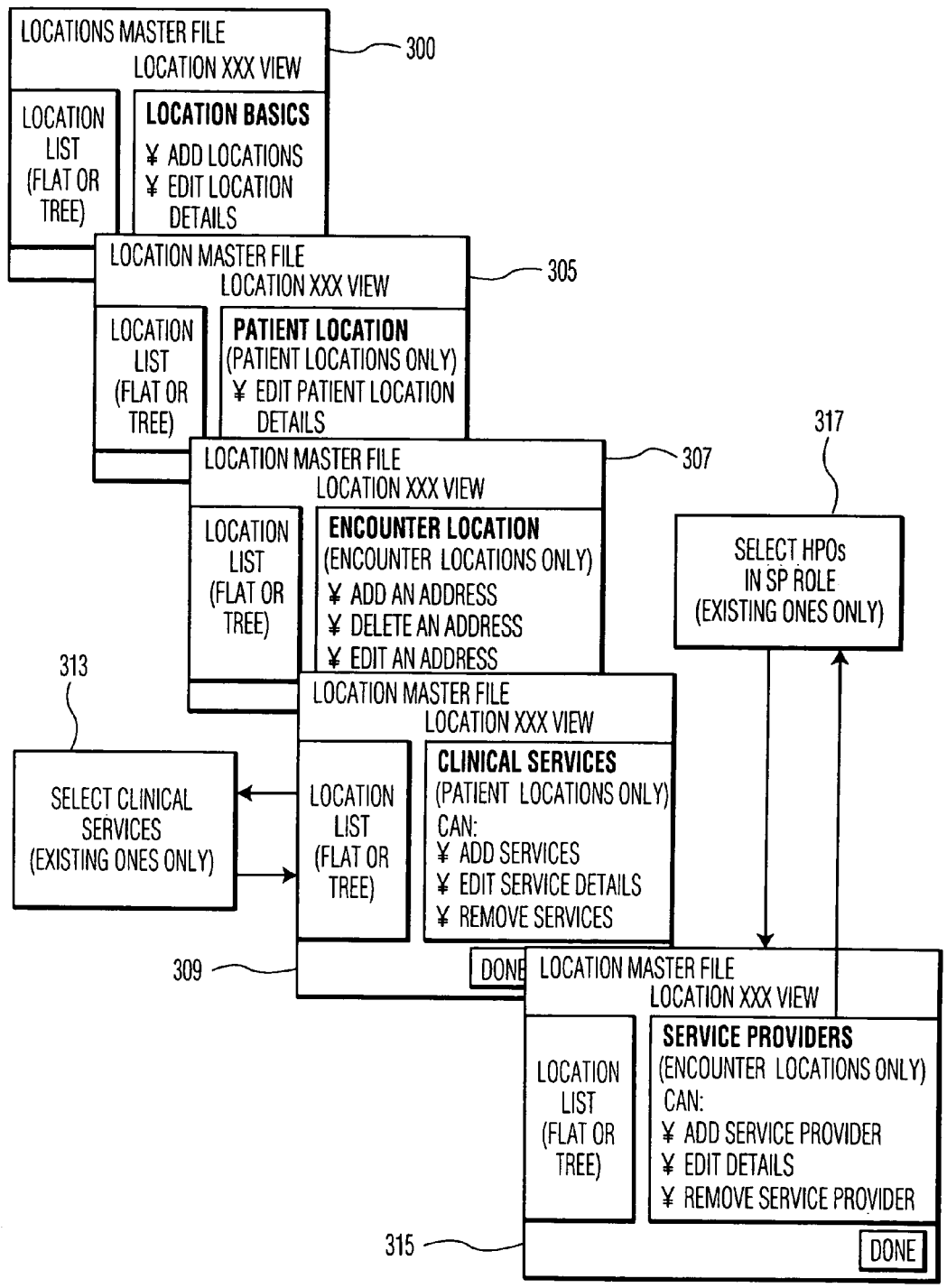
FIG. 5 shows a user interface display image navigation sequence supporting maintenance of a location structure model, according to invention principles.

FIG. 5 shows a user interface display image navigation sequence supporting maintenance of a location structure model. In response to user command, application 15 initiates generation of a display image presenting a user selected location profile master file 300. Display image 300 (and subsequent images in the FIG. 5 sequence) provides a currently selected hierarchical (tree or flat view) location profile structure representation in one window and a second window supporting profile amendment. Specifically, a window in image 300 supports user addition or deletion of a location in the current profile or editing of characteristics of a location in the current profile. Similarly image 305, which is initiated in response to a user command via image 300, includes a window supporting addition, deletion or editing of patient location information in the current profile. Image 307 (initiated in response to a user command via image 305), includes a window supporting addition, deletion or edit of encounter location information (e.g., location address information) in the current profile. Further clinical services associated with patient locations are added, edited or removed in a window in image 309 presented in response to user command via image 307. For this purpose, services may be selected for editing via generation of a service selection image (step 313) in response to user command via image 309. Similarly service providers associated with encounter locations are added, edited or removed in a window in image 315 presented in response to user command via image 309. For this purpose, service providers may be selected for editing via generation of a service provider selection image (step 317) in response to user command via image 315.

Figure 7:
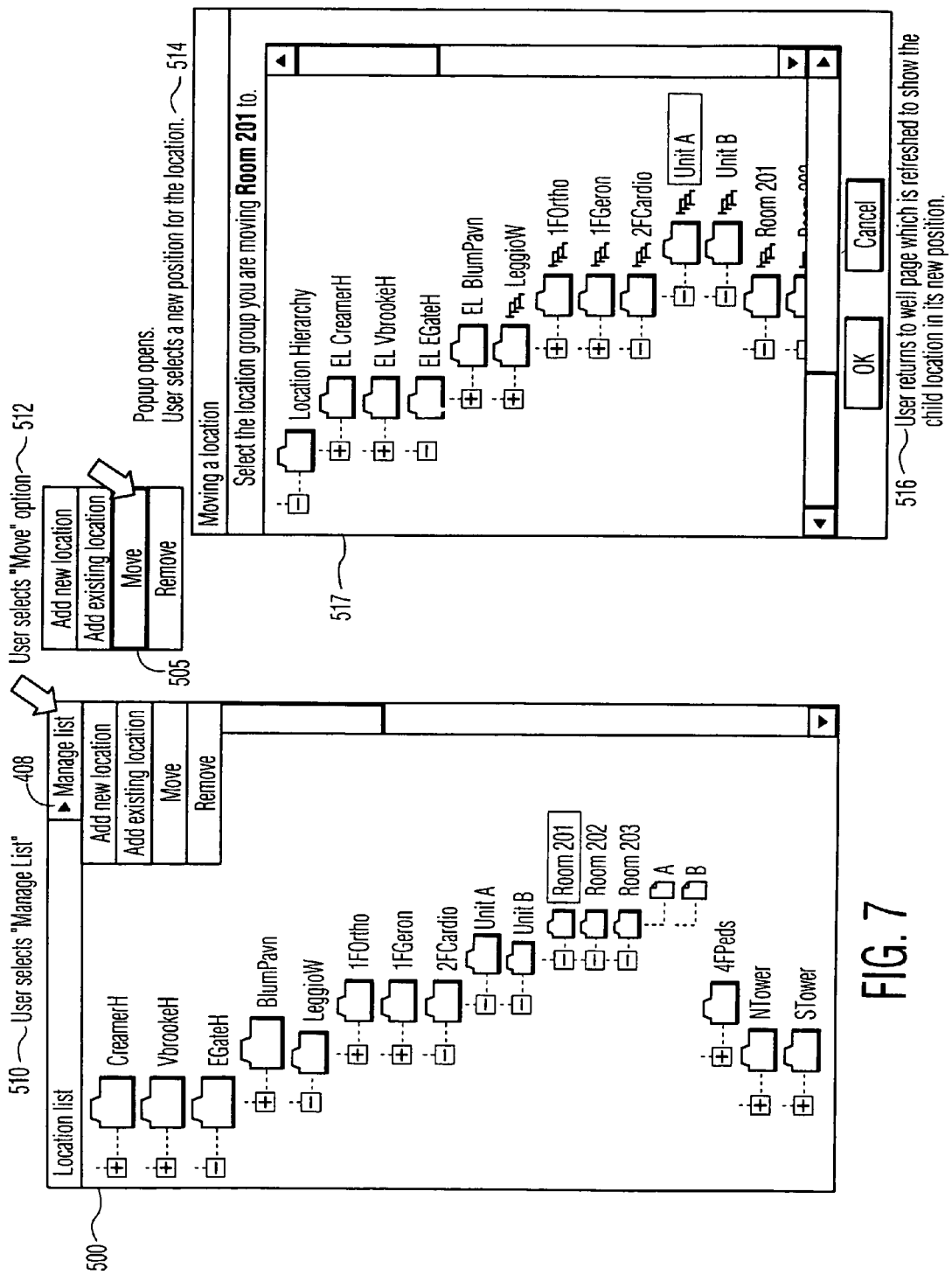
FIG. 7 shows a user interface display image navigation sequence supporting moving a location node within a particular location structure model, according to invention principles.

FIG. 7 shows a user interface display image navigation sequence supporting moving a location node within a particular location structure model. In FIG. 7 a user moves an existing item (representing room 201 in window 500) in a current profile to another point within the same location profile hierarchy. In order to do this, a user selects manage list item 408 in step 510 (e.g. from within display image 300 of FIG. 5) and selects move option 505 in step 512 from within a resulting prompt action list. The user selects existing item room 201 and selects another existing item via pop-up menu 517 (generated in step 514) to be used as a destination item (Unit A in window 517). The user further indicates if the room 201 item is to be inserted above, below, or at the same level as the destination item (Unit A). Application 15 initiates generation of a message identifying an item is to be moved as well as its intended destination and if the user confirms acceptance of the move, it is completed, and the resulting new hierarchy is displayed in step 516. If the user does not confirm acceptance, the hierarchy is left unchanged. A user follows a similar procedure in using manage list item 408 and a resulting prompt action list (step 512) to add a new or existing location or to remove a location. Application 15 initiates generation of a message indicating that the item and its subordinates are to be permanently removed from the hierarchy and a user confirms or rejects acceptance in the manner described for moving an exiting item.

In addition to supporting editing location characteristics, application 15 enables other location profile related changes. A location group may be designated as an encounter location at a past, present or future start date, for example. If no start date is specified a location group is interpreted as having continuously been a valid encounter location. A location group previously designated as an encounter location may be inactivated as an encounter location such as in response to a fire or area contamination, for example. Further, a user is able to manipulate location profile characteristic by altering start and stop dates within predetermined constraints. Also if a relationship between an encounter location and a service provider is no longer valid (e.g. through lease expiration), a user is able to delete the association between the encounter location and service provider from the profile. In addition, start and stop dates entered are validated to ensure they adhere to logical constraints. A start date of an encounter location, for example, needs to precede or be simultaneous with, a start date of an association of the encounter location with a service provider. Also a stop date of an association of an encounter location with a service provider needs to precede or be simultaneous with, the stop date of the encounter location. In order to re-associate an encounter location with an additional service provider, application 15 supports user specification of a start and/or stop date for this association or in the absence of such dates assumes that the association has been continuously valid. In contrast, in order to end a relationship between a service provider and an encounter location, a user specifies a stop date to sever the relationship between the service provider and the encounter location.

Figure 8:
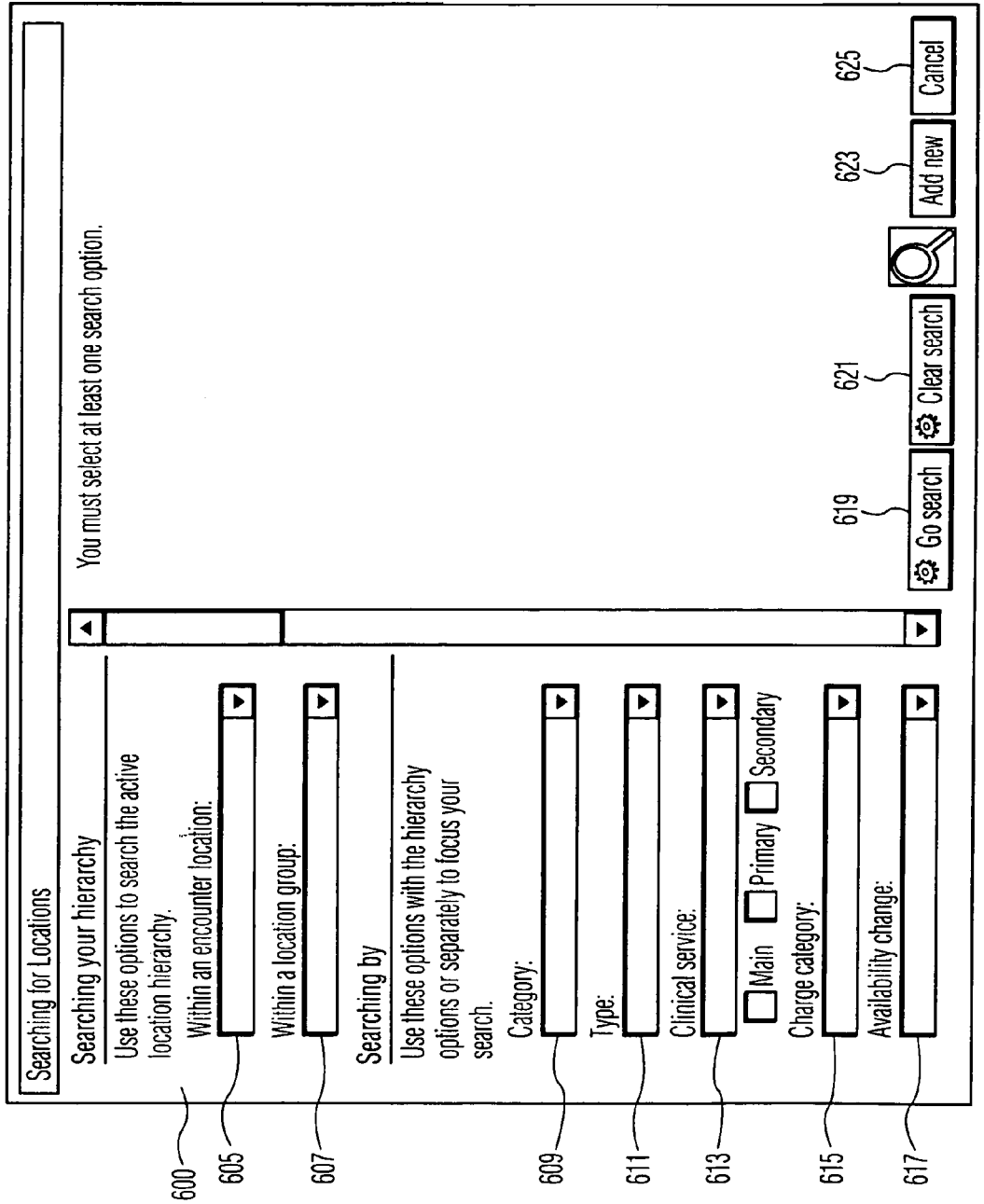
FIG. 8 shows a user interface display image menu supporting a user search for a location within a particular location structure model, according to invention principles.

FIG. 8 shows a user interface display form supporting a user search for a location within a particular location structure model. Location profile information is used to track patient movement throughout a health system and the FIG. 8 display interface form is used to facilitate user selection of an appropriate location to accommodate a patient for a particular purpose. The FIG. 8 form is also used to identify location profile information needing modification or update and to populate a list identifying location information items to be updated in a maintenance user interface image. A user enters search criteria in window 600 via prompt elements 605-617. Application 15 conducts a profile search based on a single criterion or a combination of multiple criteria in response to a user initiating a search via icon 619. Further, a user may clear the criteria via selection of icon 621 and enter different criteria. Alternatively, a user may select icon 623 to bypass the search and initiate location profile update and maintenance in an "Add mode" or cancel the search screen via icon 625.

FIG. 9 shows a user interface display image menu supporting a user search for a location within a particular location structure model including a comprehensive set of search prompt elements. Prompt elements 705-729 support user entry of search criteria including:

Organization associated with a target location
Encounter location for a target location
A patient location and associated location group
Target location type (e.g. floor, bed, room, wing)
Clinical service and type, primary, secondary, or both (ICU, Cardiology, Maternity, etc)
Target location level of care
Target location name
Target location identifier or short name
Locations recommended for use as private location
Locations recommended for VIP use
Locations by gender
Locations by availability (e.g. out of service)
Locations by occupied status (e.g. occupied only, unoccupied only, all)
Availability for pending location assignments
Availability for location assignment
All pending location assignments for a given location
All locations for a given location
Patient characteristics (Gender, Age, and Diagnosis)
Accommodation type (private, semi-private, etc)
Bed type (Regular, Sand, Air, Water)
Facility indicator—finding of locations that are defined as facilities
Only those locations that are defined as Not to be Occupied with all or specific reasons
Only those locations requiring housekeeping Only those locations that are reserved
Only those locations that have pending assignments
Application 15 further advantageously qualifies received user entered search criteria with associated business process criteria in searching location profile information to identify a candidate location. Specifically, application 15 examines the particular type of business process a user is currently engaged in and filters search results or adds business process type search criteria to ensure identified location results (i.e., location groups and/or patient locations) returned to a user concern this particular business process. For example, if a user is engaged in scheduling an encounter, search results are filtered to return location groups associated with an encounter scheduling process. Similarly, if a user is engaged in admitting a patient, search results are filtered to return location groups associated with a patient admission process.

FIG. 10 shows a composite user interface display image supporting a user search for a location within a particular location structure model in a first window 900 and location search results in a second window 920. This search form is usable to identify candidate locations for a desired patient activity such as for patient movement tracking, reporting functions and maintenance, location management and may also be used to schedule activities and to allocate appropriate charges based on charge category or level of care codes. The FIG. 9 form may additionally be used to add an existing location to a location profile (e.g., in response to user selection of "Add existing location" option in FIG. 7 "Manage list" menu of step 512). It allows previously defined location information (defined in a location maintenance operation, for example) to be added to a location profile hierarchy. The FIG. 9 user interface display image prompts user selection of search criteria 902-913 in search window 900 and results are displayed in window 920 in response to initiation of a search via icon 925. If a user sets Category parameter 904 to "Patient Location," Type field 906 is enabled and a list of user-defined patient location types is loaded into the Type filed 906 prompt list. If a user sets Category parameter 904 to "Location group" or "Encounter location", Type field 906 is enabled and a list of user-defined location group types is loaded into Type field 906 prompt list and clinical service field 910 and gender field 913 are inactivated. A location shown in search result window 920 is added to a profile hierarchy in response to user selection of an item (e.g., 304A) and selection of a resulting confirmation prompt (e.g., an OK icon). Details concerning the selected item are shown in window element 923.

When a patient vacates a location, the location may be advantageously designated in a location profile by application 15 as dirty and to automatically alert housekeeping that the patient has left the location and that the location requires cleaning before a new patient can occupy the space. A location profile master file is configurable by a user to indicate (or to prompt a user to indicate) a location is to be designated as dirty upon one or more conditions. The default condition indicator for a single occupancy patient location is "dirty" and for a multiple occupancy patient location is "not dirty."

Billing charges such as for operational overhead and nursing time are based on a location a patient is occupying. The charge for a location is based on the nature of the patient encounter occurring there. Application 15 advantageously uses a location profile in tracking and reporting billing based on characteristics including, Encounter Type, Clinical Service provide during an encounter, a Level of Care of an encounter and encounter Duration (Days or Hours). Thereby application 15 supports billing at a higher rate when a patient is occupying a location requiring a correspondingly higher level of care. For instance, a private room typically has a higher charge than a semi-private room and a room in an intensive care unit (ICU) costs more than a room on a medical or surgical floor. Application 15 also supports report generation for billing, statistical and trend analysis. For this purpose locations are sorted by location condition or license status to aid the user in statistical reporting and trend analysis. Sorting by condition applies to patient locations of different type and involves sorting by indicators identifying one or more of the following location characteristics.

Clean—The location is Ready for use.

Dirty—Indicated location has not been cleared for use since last occupied.

Occupied—Patient(s) currently occupy the location which has reached its Maximum Occupancy.

Unoccupied—The location, which may or may not have patients occupying it, has not reached its Maximum Occupancy.

Reserved—The location is not occupied but is being held for an anticipated patient placement.

Out of service—the location is not available for use for a specified time period Fumigation required Maintenance/repairs required Staffing issue Construction/renovation In service—the location is available for use within the organization Occupancy modified—the maximum occupancy of the location has been modified, either to increase or decrease the previous occupancy.

Sorting by license status enables reports to be derived that include only licensed, unlicensed, or both statuses of locations.

The systems, processes and user interface forms presented in FIGS. 1-10 are not exclusive. Other systems, processes and user interface forms may be derived in accordance with the principles of the invention to accomplish the same objectives. The inventive principles may be applied in a variety of environments for identifying and tracking location related information and to facilitate set-up, maintenance and operation of an organization structure and re not constrained to be used in the healthcare field. Specifically, the inventive principles are applicable to manage location information and associated personnel and contents wherever location structure or configuration alteration or location complexity pose a burden.

What is claimed is:

1. A method for processing location related information for use in facilitating movement of a patient in a healthcare enterprise, comprising the steps of:

establishing a profile comprising information enabling a search to identify a plurality of locations available for use by a patient for different purposes and including rooms supporting patient treatment and patient stay, said profile identifies a hierarchical organization of locations within a healthcare enterprise for at least one of (a) hosting a patient encounter with a healthcare enterprise involving patient and healthcare enterprise interaction, and (b) accommodating a patient for a variable duration;

storing said profile and an associated date of validity of said profile;

incorporating in said profile attributes including, a location type identifier, and a location characteristic of clinical significance influencing availability of a particular location to a patient having a particular medical condition and identifying a level of care indicative of frequency of clinician intervention in patient care supported by a location including rooms supporting patient treatment and patient stay suitable for a patient having said particular medical condition; and employing said profile in providing a user with an indication of location availability in response to user command.

2. A method according to claim 1, wherein said level of care is indicative of urgency of clinician intervention in patient care supported by a location, and including the step of
   filtering search results identifying candidate locations in response to a business process type associated with the search and wherein
   said profile comprises information identifying a plurality of patient locations available to accommodate a patient for different purposes.

3. A method according to claim 1, wherein
   said profile supports tracking movement of a patient throughout a healthcare enterprise and
   said location type identifier includes information identifying (a) location characteristics and (b) location facilities.

4. A method according to claim 3, wherein
   said location characteristics information comprises information identifying at least one of, (a) furnishing items in a location and (b) function associated with a location.

5. A method according to claim 3, wherein
   said location facilities information comprises information identifying at least one of, (a) medical equipment available at a location, (b) a gender restriction of a location, (c) a cleaning indicator identifying a location is to be cleaned upon occurrence of a condition, (d) an age range restriction of a location and (e) a billing code identifying a billing category of a location.

6. A method according to claim 1, wherein
   said location type identifier identifies a location within said plurality of locations and said plurality of locations include at least two of, (a) a patient room, (b) a hospital waiting room, (c) a hospital department room, (d) a surgery related room, (e) a location within an identified room, (f) an identified room in an identified building inside said enterprise and (g) a location outside said enterprise.

7. A method according to claim 6, wherein
   said hospital department room comprises one of (i) a radiology room, (ii) a laboratory room, (iii) a pharmacy room, (iv) a room designated for performing a clinical test of a patient, (v) a room designated for performing patient examination (vi) a room designated for performing an administrative function, (vii) an inpatient room (viii) an outpatient room and (ix) an emergency room.

8. A method according to claim 1, wherein
   said location characteristic of clinical significance includes information identifying a level of care category associated with a location, said level of care is indicative of urgency of clinician intervention in patient care supported by a location.

9. A method according to claim 1, wherein
   said location characteristic of clinical significance identifies at least one of (a) whether a location is sterile, and (b) medical facilities available at a location.

10. A method according to claim 1, including the step of incorporating an attribute in said profile for identifying a maximum capacity of person occupancy of a location.

11. A method according to claim 1, including the steps of
    selecting a treatment location different to a patient bed location for occupancy by a particular patient via a displayed user interface image in response to user command.

12. A method according to claim 11, including the steps of
    selecting a location for occupancy by a particular patient via a displayed user interface image in response to user command, and
    receiving an indication a patient has occupied said selected location.

13. A method according to claim 1, including the step of
    incorporating an attribute in said profile for identifying billing information of a particular location including identifying at least one of (a) whether occupancy in said particular location is to be billed for, (b) how occupancy in said particular location is to be billed for, and (c) how billing for individual occupants of a multiple occupancy location is to be performed.

14. A method according to claim 1, including the step of
    incorporating an attribute in said profile for identifying occupancy nature of a particular location including identifying at least one of (a) whether a location is designated for a transient patient stay, (b) a length of anticipated patient stay and (c) whether a location is designated for a multi-day patient stay.

15. A method according to claim 1, wherein
    in said step of establishing a profile comprising information identifying a plurality of locations available to accommodate a patient for different purposes,
    said different purposes include at least two of (a) patient healthcare administration, (b) patient clinical evaluation and (c) patient treatment.

16. A method for managing location related information for use in facilitating movement of a patient in a healthcare enterprise, comprising the steps of:
    establishing a first profile comprising information identifying a plurality of locations within a first physical structure, said plurality of locations being available to accommodate a patient for different purposes, said first profile identifies a hierarchical organization of locations within a healthcare enterprise for at least one of (a) hosting a patient encounter with a healthcare enter rise involving patient and healthcare enterprise interaction, and (b) accommodating a patient for a variable duration;
    storing said first profile and an associated date of validity of said first profile;
    incorporating in said first profile attributes including,
        a location type identifier, and
        a location characteristic of clinical significance influencing availability of a particular location to a patient having a particular medical condition and identifying a level of care indicative of frequency and urgency of clinician intervention in patient care supported by a location including rooms supporting patient treatment and patient stay suitable for a patient having said particular medical condition; and
    establishing a second profile incorporating information from said first profile, said second profile comprising information identifying a plurality of locations within a second physical structure derived by modifying said first physical structure.

17. A method according to claim 16, including the steps of
    storing said first profile and
    associating location information common to said first and second profiles using at least one of, (a) common location identifiers and (b) a map linking location identifiers of said first profile to location identifiers of said second profile.

18. A method according to claim 16, including the steps of
    date stamping said first profile to indicate at least one of, (a) a last date and (b) a first date, said first profile was valid, and
    storing said date stamped first profile.

19. A method for processing location related information for use in facilitating movement of a patient in a healthcare enterprise, comprising the steps of:

establishing a profile comprising information identifying a hierarchical organization of locations enabling a search to identify locations available for use by a patient for different purposes within a healthcare enterprise and including rooms for, (a) hosting a patient encounter with a healthcare enterprise involving patient and healthcare enterprise interaction supporting patient treatment, and (b) accommodating a patient during an inpatient stay;

storing said profile and an associated date of validity of said profile;

incorporating in said profile attributes including,
   a location type identifier, and
   a location characteristic of clinical significance influencing availability of a particular location to a patient having a particular medical condition and identifying a level of care indicative of the urgency of clinician intervention in patient care supported by a location including rooms supporting patient treatment and patient stay suitable for a patient having said particular medical condition;

filtering search results identifying candidate locations in response to a business process type associated with the search; and employing said profile in providing a user with an indication of location availability in response to user command.

20. A method according to claim 19, including the step of employing said profile in finding information concerning a particular location in response to user entered search criteria.

21. A method according to claim 19, including the step of initiating generation of a message for triggering a location maintenance function in response to information identifying a change in said profile comprising at least one of, (a) a change in location availability, (b) a change in location occupancy and (c) a change in location condition.

22. A method according to claim 19, including the step of employing said profile in generating billing information.

23. A method according to claim 19, including the step of employing said profile in generating a report identifying location usage information.

24. A method according to claim 19, including the step of incorporating in said profile information associating a location with services provided at said location.

25. A method according to claim 19, wherein said level of care is indicative of the frequency of clinician intervention in patient care supported by a location.

* * * * *